United States Patent
Schuetz et al.

(10) Patent No.: US 10,316,055 B2
(45) Date of Patent: Jun. 11, 2019

(54) CRYSTALLIZATION OF 25-HYDROXY-7-DEHYDROCHOLESTEROL

(71) Applicant: DSM IP Assets B.V., Heerlen (NL)

(72) Inventors: Jan Schuetz, Kaiseraugst (CH); Ralph Waechter, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 15/774,697

(22) PCT Filed: Nov. 28, 2016

(86) PCT No.: PCT/EP2016/079013
§ 371 (c)(1),
(2) Date: May 9, 2018

(87) PCT Pub. No.: WO2017/093192
PCT Pub. Date: Jun. 8, 2017

(65) Prior Publication Data
US 2018/0327442 A1   Nov. 15, 2018

(30) Foreign Application Priority Data
Nov. 30, 2015   (EP) .................................... 15197036

(51) Int. Cl.
*C07J 9/00* (2006.01)
*B01D 9/00* (2006.01)

(52) U.S. Cl.
CPC ............... *C07J 9/00* (2013.01); *B01D 9/005* (2013.01); *B01D 9/0063* (2013.01); *B01D 2009/0086* (2013.01)

(58) Field of Classification Search
CPC ..... C07J 9/00; B01D 9/005; B01D 2009/0086
See application file for complete search history.

(56) References Cited

U.S. PATENT DOCUMENTS 4,116,985 A * 9/1978 Salmond .................... C07J 9/00
552/504

FOREIGN PATENT DOCUMENTS

CN     104 910 231    9/2015
WO     WO 93/21204    10/1993

OTHER PUBLICATIONS

Hursthouse et al, Organic Process Research & Development, Why Do Organic Compounds Crystallize Well or Badly or Ever so Slowly? Why is Crystallization Nevertheless Such a Good Purification Technique?, 2009, 13, 1231-1240. (Year: 2009).*
Schul'man et al, Journal of Organic Chemistry USSR, Production of derivatives of provitamin D3 with modified side chain structure, 1988, 24(11), pp. 2111-2115. (Year: 1988).*
Staples, Growing and Mounting Crystals Your Instrument Will Treasure,2017, pp. 1-17, recovered from https://www2.chemistry.msu.edu/facilities/crystallography/xtalgrow.pdf on Aug. 23, 2018 (Year: 2017).*
International Search Report for PCT/EP2016/079013, dated Jan. 27, 2017, 3 pages.
Written Opinion of the ISA for PCT/EP2016/079013, dated Jan. 27, 2017, 8 pages.
Shul'man, et al., "Production of derivatives of provitamin D3 with modified side chain structure", Journal of Organic Chemistry USSR, vol. 24, No. 11, 1988, pp. 2111-2115.
Shul'man, et al., "Synthesis of Hydroxylated Group D Provitamin Derivatives", Journal of General Chemistry USSR, vol. 58, No. 1, 1988, pp. 191-198.
Jin et al., "Synthetic method of 25-hydroxy-7-dehydrocholesterol", XP002756140, retrieved Apr. 4, 2016, 12 pages.
Moiseenkov et al., "Partial Synthesis of 25-Hydroxycholesterol and 25-Hydroxyprovitamin D3 using a Cyclopropyl Carbinyl Rearrangement", J. Bioorganic Chemistry USSR, vol. 9, No. 1, 1983, pp. 72-75.

* cited by examiner

*Primary Examiner* — Paul A Zucker
(74) *Attorney, Agent, or Firm* — Nixon & Vanderhye P.C.

(57) ABSTRACT

The present invention relates to a method of purification of compound of formula (I) which comprises the step of crystallization of compound of formula (I) from a composition comprising the compound of formula (I) and the compound of formula (II) and a specific solvent system containing ethanol, 1-propanol, 2-propanol, 2-methyl-1-propanol, 1-butanol or 2-butanol.

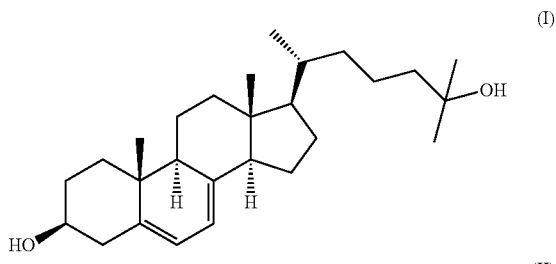

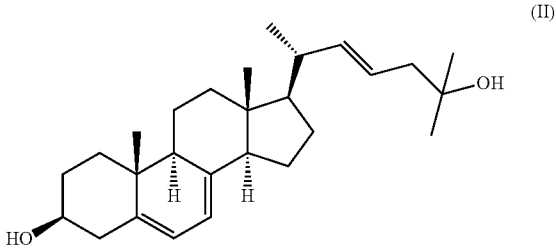

13 Claims, No Drawings

CRYSTALLIZATION OF 25-HYDROXY-7-DEHYDROCHOLESTEROL

This application is the U.S. national phase of International Application No. PCT/EP2016/079013 filed 28 Nov. 2016, which designated the U.S. and claims priority to EP Patent Application No. 15197036.5 filed 30 Nov. 2015, the entire contents of each of which are hereby incorporated by reference.

TECHNICAL FIELD

The present invention relates to the field of vitamin D, particularly to 25-hydroxy-vitamin D3 (=HyD), respectively to its precursor of formula (I) (=25-Hydroxy-7-dehydrocholesterol) (=HyDHC).

BACKGROUND OF THE INVENTION

Compound of formula (I) (=HyDHC) is an important intermediate in the synthesis of 25-hydroxy-vitamin D3 (=HyD) (=Calcidiol).

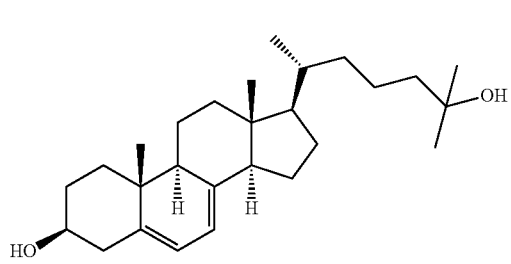

Compound of formula (I) can be synthesized in a multi-step synthesis from desmosterol or from the corresponding Cholesta-5,7,24-trien-3β-ol using a Diels-Alder adduct as disclosed in WO 93/21204 A1.

It has been observed that compound of formula (I) comprises relative high amounts of the impurity of formula (II) (=3β-Cholesta-5,7,22-triene-3,25-diol)

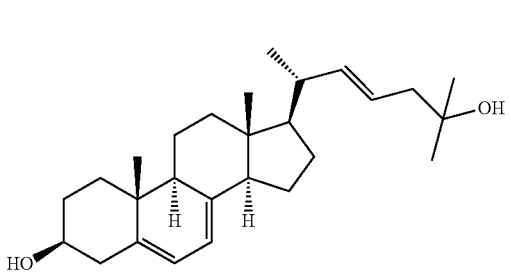

As this compound of formula (II) differs only by a C=C double bond (at carbon position 22) from compound of formula (I) the two compounds have very similar physical properties.

As compound (I) is transformed to 25-hydroxy-vitamin D3 (=HyD) using a photochemical reaction step, also the impurity, i.e. compound of formula (II), is transformed analogously to an impurity in the targeted end product (HyD).

Therefore, it is desired to avoid or strongly reduce such impurities in the end product.

SUMMARY OF THE INVENTION

Therefore, the problem to be solved by the present invention is to provide an efficient method of purification of HyDHC and strongly reduce its amount of the impurity of formula (II).

Surprisingly, it has been found that HyDHC can be purified by method of purification according to claim 1. In particular, is has been found that a crystallization using a unique solvent system can offer a solution to said problem.

Further aspects of the invention are subject of further independent claims. Particularly preferred embodiments are subject of dependent claims.

It is very surprising that the compounds of formula (I) and (II) can be separated from each other by means of crystallization as particularly the two molecules are very similar to each other. Both compounds have two alcohol groups which are spaced by a bulky hydrophobic $C_{22}$-enties which differ only by the existence of a single carbon-carbon double bond located very far from the two hydroxyl groups.

DETAILED DESCRIPTION OF THE INVENTION

In a first aspect the present invention relates to method of purification of compound of formula (I) which comprises the step of crystallization of compound of formula (I) from a composition comprising the compound of formula (I) and the compound of formula (II)

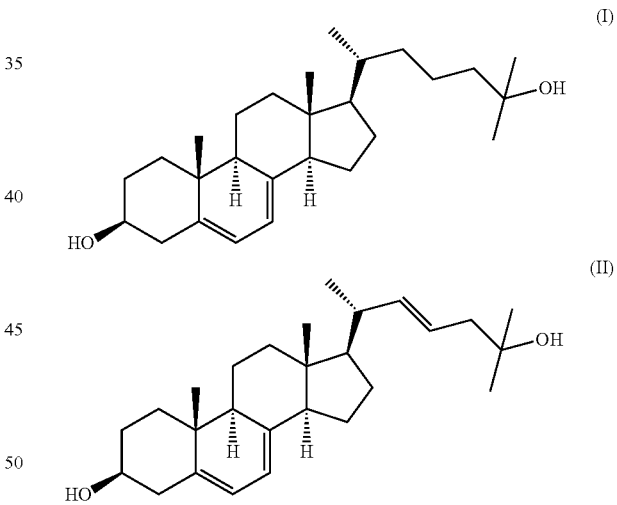

and a solvent system
characterized in that the solvent system is either
i) ethanol or 1-propanol or 2-propanol or 2-methyl-1-propanol or 1-butanol or 2-butanol;
or
ii) a binary or tertiary or quaternary mixture of ethanol or 1-propanol or 2-propanol or 2-methyl-1-propanol or 1-butanol or 2-butanol;
or
iii) a mixture of at least one of the solvents of the group consisting of ethanol, 1-propanol, 2-propanol, 2-methyl-1-propanol, 1-butanol and 2-butanol with methanol and/or with a $C_5$-$C_6$ alcohol, with the proviso that the total amount of ethanol and 1-propanol and 2-propanol and 2-methyl-1-propanol and 1-butanol and 2-butanol is equal or more than 50% by weight of the solvent system.

"HyDHC" is used in the present document as an abbreviation for compound of formula (I).

"DDH-HyDHC" is used in the present document as an abbreviation for compound of formula (II).

All indication of % in this document are % by weight unless indicated otherwise.

It is very surprising that the compounds of formula (I) and (II) can be separated from each other by means of crystallization.

Compound of formula (II) is an impurity being present in the production of compound (I).

The present process relates to a crystallization of compound from a solvent system.

The term "solvent system" relates either to a single solvent or a mixture of solvents.

We have found the three different embodiments of such a solvent system to be effective in said purification process:

i) ethanol or 1-propanol or 2-propanol or 2-methyl-1-propanol or 1-butanol or 2-butanol;
or
ii) a binary or tertiary or quaternary mixture of ethanol or 1-propanol or 2-propanol or 2-methyl-1-propanol or 1-butanol or 2-butanol;
or
iii) a mixture of at least one of the solvents of the group consisting of ethanol, 1-propanol, 2-propanol, 2-methyl-1-propanol, 1-butanol and 2-butanol with methanol and/or with a $C_5$-$C_6$ alcohol, with the proviso that the total amount of ethanol and 1-propanol and 2-propanol and 2-methyl-1-propanol and 1-butanol and 2-butanol is equal or more than 50% by weight of the solvent system.

In all these three embodiments the key point is the mandatory presence of at least ethanol or 1-propanol or 2-propanol or 2-methyl-1-propanol or 1-butanol or 2-butanol.

It has been found that the separation is no longer possible or at least very much less effective if a different solvent system is used.

Particularly, it has been shown that neither methanol nor higher (higher than $C_5$) alcohols are suitable for use as sole solvent in the solvent system.

In a preferred embodiment of solvent system i) the solvent system used for crystallization is ethanol or 1-propanol or 2-propanol.

In a more preferred embodiment of solvent system i) the solvent system used for crystallization is 2-propanol.

In a preferred embodiment of solvent system ii) the solvent system used for crystallization a binary or tertiary mixture of ethanol or 1-propanol or 2-propanol. It is preferred that 2-propanol is part of the binary or tertiary mixture and that particularly the amount by weight of 2-propanol is the major part by weight of such a solvent system.

In a very preferred embodiment of solvent system ii) the solvent system used for crystallization is a binary mixture of ethanol and 2-propanol. It is preferred that the weight ratio of 2-propanol:ethanol is lower than 1.

In a preferred embodiment of solvent system iii) the solvent system used for crystallization is a mixture either of
methanol and 2-propanol (=methanol/2-propanol)
of
methanol and 1-propanol (=methanol/1-propanol)
or of
methanol and 1-propanol and 2-propanol (=methanol/1-propanol/2-propanol)
or of
methanol and ethanol and of 2-propanol (=methanol/ethanol/2-propanol), particularly a mixture of methanol and 2-propanol.

As already mentioned above in any solvent system iii) there is the proviso that the total amount of ethanol and 1-propanol and 2-propanol is equal or more than 50% by weight of the solvent system In a preferred embodiment the solvent system used for crystallization is a mixture of at least one of the solvents of the group consisting of ethanol, 1-propanol, 2-propanol, 2-methyl-1-propanol, 1-butanol and 2-butanol with methanol and/or with a $C_5$-$C_6$ alcohol, with the proviso that the total amount of ethanol and 1-propanol and 2-propanol and 2-methyl-1-propanol and 1-butanol and 2-butanol is more than 60% by weight, particularly more than 65% by weight, preferably more than 70% by weight, more preferably more than 75% by weight Crystallization is a known process of purification per se. Particularly easy to be separated are molecules of different structures. However, it is known that the separation of molecules, particularly molecules of higher molecular weights, which have the same functional groups and similar structure are very difficult to be separated by crystallization.

More specifically the above described method of purification comprises the steps a) dissolving composition comprising compound of formula (I) and compound of formula (II) at temperature ($T_{sol}$) above 40° C. in the solvent system used for the crystallization to yield a solution A comprising compound of formula (I) and of formula (II) compound b) cooling solution A comprising compound of formula (I) and of formula (II) compound obtained by step a) to a temperature ($T_{cool}$) of 30° C. or below to yield crystals of compound of formula (I)

c) isolating crystals of compound of formula (I).

Particularly, the temperature ($T_{sol}$) in step a) is above 60° C., particularly at the boiling temperature of the solvent system or at a temperature being at most 10° C., preferably at most 5° C., lower than the boiling temperature of the solvent, whereas the boiling temperature of the solvent is measured at 1013 mbar.

It is preferred to bring to use reflux of the solvent or of the solvent having the lowest boiling point in case a solvent mixture is used as solvent system.

For a most efficient crystallization it is preferred that the amount of the specific composition comprising compound of formula (I) and compound (II) is selected in step a) as high as possible resulting in a still clear solution at said temperature.

On cooling the solution A in step b) the solution gets supersaturated and finally crystals of compound of formula (I) are formed which are isolated in step c).

As an isolation method for step c) a variety of methods can be used. Particularly, the crystals of compound of formula (I) are isolated by filtration or centrifugation. Most preferably the crystals of formula (I) are isolated by filtration.

It is, furthermore, preferred that during step b), particularly in the first phase of the cooling, seed crystals are added (inoculation) to the solution A, to initiate crystal growths.

It is preferred that the temperature ($T_{cool}$) in step b) is in the range of −10° C. to 15° C., particularly in the range of 0° C. to 10° C.

It is preferred, that the temperature difference between the temperature of dissolving, i.e. temperature $T_{sol}$, in step a) and the temperature obtained by the cooling step b), i.e. temperature after cooling $T_{cool}$, is at least 20K, more preferably at least 40 K, even more preferably at least 50 K, most preferably at least 60 K.

The duration of keeping the composition and solvent system at the dissolving temperature $T_{sol}$ in step a) is preferably selected so that it is assured that the maximum amount of composition is dissolved at said temperature.

The cooling rate in step b) is preferably selected so to get a sound balance between slow cooling to allow good purification quality and fast cooling to get a cheap process (economic consideration). Typically a cooling rate if 1-20 K/hour, particularly 5-10 K/hour, showed to yield a good purification as well as acceptable handling (work/equipment) cost for the crystallization process.

As in any purification process, one starts from a composition of different substances, in the present case from a composition comprising the compound of formula (I) and the compound of formula (II). After the purification, the desired compound, in the present case compound of formula (I), is present in a higher purity, i.e. the amount of undesired compounds (=impurities) in the desired compound is reduced as compared to the situation before purification. In the present case the impurity is compound of formula (II).

It is, therefore, clear to any person skilled in the art, that the crystals of formula (I) still comprise impurities in the form of compound of formula (II). However, the amount of this impurity of formula (II) in the crystals of compound of formula (I) is significant lower as compared to the situation in the original composition comprising of compound of formula (I) and compound of formula (II) prior to the purification.

By the crystallization compound of formula (II) is accumulated in the mother liquor, which is obtain in step c) after the isolation of crystals of compound of formula (I).

As a mean for assessing the efficiency of purification the following parameters $C_{II,cryst}$, $C_{II,cryst}$ and $r_{ML/cryst}$ can be taken into account:

$C_{II,cryst}$=concentration of DDH-HyDHC in crystals of HyDHC $C_{II,ML}$=concentration of DDH-HyDHC in the mother liquor $$r_{ML/cryst} = \frac{C_{II,ML}}{C_{II,cryst}}$$

The amount of compound (II) can be determined by HPLC/MS of either the crystals of HyDHC or the mother liquor.

The lower $C_{II,cryst}$ is, the purer the crystals of compound of formula (I) are. The higher $C_{II,ML}$ is, the more efficiently compound of formula (II) is separated by means of the solvent system.

For an industrial process it is preferable that the yield of crystallization, i.e. the weight ratio of amount of compound of formula (I) (=HyDHC) after the crystallization to the amount of compound of formula (I) prior the crystallization is as high as possible.

Therefore, in a preferred embodiment, the method of purification of does not only result in crystals of compound of formula of formula (I) in high purity but also to a high yield of crystallization, in case of 2 or more crystallization cycles to high overall yield of crystallization.

By re-crystallizations the purification can be improved. Therefore, using a method of purification which has 2 or more crystallization cycles can increase further the degree of purification. Here for any additional recrystallization, the crystals of formula (I) isolated in step c) are dissolved in the solvent system at the temperature ($T_{sol}$) of step a), followed by step b) and c).

However, as any additional recrystallization is increasing significantly the cost of purification, it is preferred to have a purification process having a purification as high as possible using a single crystallization.

It is preferred to the method of purification as described above results in purified compound of formula (I) comprising compound of formula (II) as impurity in an amount of less than 0.40% by weight, preferably less than 0.20% by weight, more preferably less than 0.15% by weight, even more preferably less than 0.10% by weight, most preferably less than 0.07% by weight, relative to the weight of compound of formula (I).

Therefore, in a second aspect, the present invention relates to a composition comprising the compound of formula (I) and the compound of formula (II), characterized in that the amount of compound of formula (II) is at most 0.40% by weight, preferably at most 0.20% by weight, more preferably at most 0.15% by weight, even more preferably at most 0.10% by weight, most preferably less at most 0.07% by weight, relative to the weight of compound of formula (I).

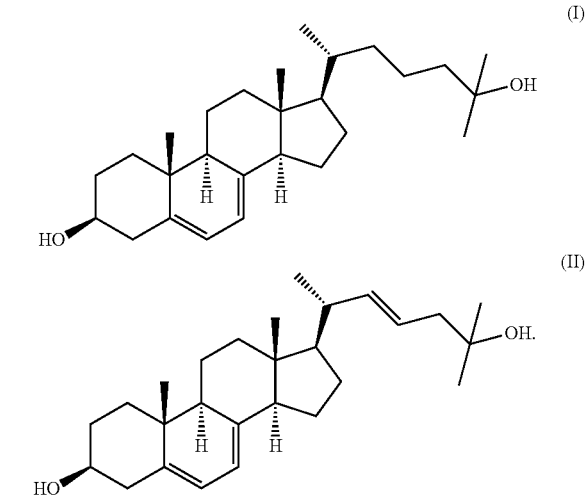

In a further aspect, the present invention relates to the use of a solvent system being either i) ethanol or 1-propanol or 2-propanol or 2-methyl-1-propanol or 1-butanol or 2-butanol;

or ii) a binary or tertiary or quaternary mixture of ethanol or 1-propanol or 2-propanol or 2-methyl-1-propanol or 1-butanol or 2-butanol;

or iii) a mixture of at least one of the solvents of the group consisting of ethanol, 1-propanol, 2-propanol, 2-methyl-1-propanol, 1-butanol and 2-butanol with methanol and/or with a $C_5$-$C_6$ alcohol, with the proviso that the total amount of ethanol and 1-propanol and 2-propanol and 2-methyl-1-propanol and 1-butanol and 2-butanol is equal or more than 50% by weight of the solvent system.
for the crystallization of compound of formula (I)

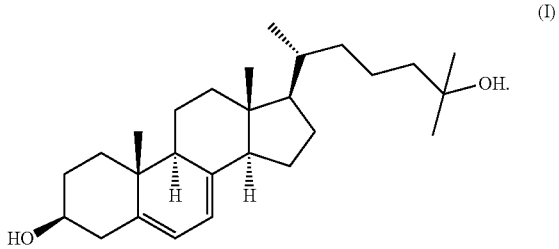

We have shown above in great detail that said solvent system can be used very efficiently for the purification of compound (I) involving a crystallization.

Also the preferred embodiments of such a solvent system have been already shown in great detail.

EXAMPLES

The present invention is further illustrated by the following experiments.

Experimental Methods

The amounts of compound of formula (II) (=DDH-HyDHC) are determined by HPLC/MS:

Column: polar modified silica, injection vol. 50 μl, eluent: tert.-butylmethylether/methanol=10/90, detection 284 nm+MS Detector.

Retention times: HyDHC: 19.5 min., DDH-HyDHC: 16.5 min.

Experimental Series 1: Crystallization from Different Solvents 1 g of HyDHC crystals having an impurity 0.5% DDH-HyDHC has been dissolved under stirring in the respective amount of the solvent system as indicated in table 1 in a glass flask at reflux temperature of the solvent system to yield a homogenous solution. The amount of solvent system was selected to obtain a clear solution aiming at maximal concentration of HyDHC.

The stirring has been stopped and the solution has been cooled down at a cooling rate of 10 K/h to 20° C. (=$T_{cool}$). During the cooling down the solution has been inoculated every 30 minutes by adding individual crystal seeds of HyDHC.

Finally the crystals formed have been separated by filtration over a D3 sintered glass frit under reduced pressure and dried until the weight of the crystals remained constant.

The amount of DDH-HyDHC has been determined in the crystals of HyDHC isolated, respectively in the mother liquor, and indicated as $C_{II,cryst}$ respectively as $C_{II,ML}$ as in table 1.

TABLE 1

Crystallization using different kind of solvent systems.

| Example | Solvent system (vol./vol.) | Volume solvent system [ml] | $C_{II,cryst}$ | $C_{II,ML}$ | $r_{ML/cryst}$ |
|---|---|---|---|---|---|
| 1 | IPA | 30 | 0.38% | 0.94% | 2.5 |
| 2 | IPA/MeOH (30/5) | 35 | 0.3% | 1.06% | 3.5 |
| 3 | IPA/MeOH (20/20) | 40 | 0.38% | 1.16% | 3.1 |
| 4 | IPA/MeOH (40/4) | 44 | 0.39% | 0.93% | 2.4 |
| 5 | EtOH | 30 | 0.36% | 1.0% | 2.8 |
| Ref. 1 | MeOH | 50 | 0.59% | 1.02% | 1.7 |
| Ref. 2 | THF | 15 | 0.56% | 1.2% | 2.1 |
| Ref. 3 | Toluene | 45 | 0.47% | 1.18% | 2.5 |

IPA = 2-propanol
MeOH = methanol
EtOH = ethanol
THF = tetrahydrofurane
$r_{ML/cryst} = C_{II,cryst}/C_{II,ML}$ As can be seen from the data in table 1 for the Examples 1-5 in accordance with the embodiments of the invention disclosed herein in comparison to the Comparative Examples Ref.1-Ref.3 not in accordance with the embodiments of the invention disclosed herein, the purification depends strongly from the solvent system used.

Experimental Series 2: Degree of Purification During Cooling 1 g of HyDHC crystals having an impurity 0.5% DDH-HyDHC was dissolved in 30 ml of 2-propanol at 83° C. and cooled to 0° C. (=$T_{cool}$) at a cooling rate of 10 K/h. During the cooling down the solution has been inoculated every 30 minutes by adding individual crystal seeds of HyDHC. During cooling at the temperature $T_{anal.}$, as indicated in table 2, an analytical sample of solution and crystals has been taken of which the amount of DDH-HyDHC in the crystals, respectively in the mother liquor, has been determined as in experimental series 1. The values found are indicated as $C_{II,cryst}$ respectively as $C_{II,ML}$ as in table 2.

TABLE 2

Crystallization: Degree of purification during cooling.
Example 6

| | $T_{anal.}$ | | | | | | |
|---|---|---|---|---|---|---|---|
| | 60° C. | 50° C. | 40° C. | 30° C. | 20° C. | 10° C. | 0° C. |
| $C_{II,cryst}$ | 0.36% | 0.39% | 0.37% | 0.39% | 0.38% | 0.37% | 0.31% |
| $C_{II,ML}$ | 0.52% | 0.60% | 0.65% | 0.78% | 0.85% | 0.99% | 1.64% |
| $r_{ML/cryst}$ | 1.4 | 1.5 | 1.7 | 2 | 2.2 | 2.6 | 5.3 |

$r_{ML/cryst} = C_{II,ML}/C_{II,cryst}$

As can be seen from table 2, the purification is particularly improved when the crystals are formed at very low temperatures, particularly below 10° C.

Experimental Series 3: Degree of Purification at Different End Temperature of Cooling 1 g of HyDHC crystals having an impurity 0.5% DDH-HyDHC was dissolved in 30 ml of 2-propanol at 83° C. and cooled to 20° C., or 0° C. or −20° C. at a cooling rate of 10 K/h. At 70° C. the solution has been inoculated by adding individual crystal seeds of HyDHC. After isolation of the crystals formed by filtration over a D3 sintered glass frit under reduced pressure until the weight of the crystals remained constant the amount of DDH-HyDHC has been determined in the crystals of HyDHC isolated, respectively in the mother liquor, and indicated as $C_{II,cryst}$ respectively as $C_{II,ML}$ as in table 3. Furthermore, the yield has been determined. The yield is the ratio of the weight of crystals obtained after separation to the weight of crystals used when dissolving (i.e. in this case 1 g).

TABLE 3

Crystallization: Degree of purification at different end temperature of cooling.

| Example | $T_{cool}$ (° C.) | $C_{II,cryst}$ | $C_{II,ML}$ | $r_{ML/cryst}$ | Yield [%] |
|---|---|---|---|---|---|
| 1 | 20 | 0.38 | 0.94 | 2.5 | |
| 7 | 0 | 0.31 | 1.64 | 5.3 | 79 |
| 8 | −20 | 0.35 | 2.64 | 7.6 | 86 |

$r_{ML/cryst} = C_{II,cryst}/C_{II,ML}$

The results of table 3 show that using a very low end temperature of cooling ($T_{cool}$) is very advantageous in view of optimizing purity and of yield already for a single crystallization.

Experimental Series 4: Degree of Purification at Different End Temperature of Cooling In another experiment 1 g of HyDHC crystals having an impurity 0.5% DDH-HyDHC has been dissolved under stirring in the respective amount of the solvent system as indicated in table 4 in a glass flask at reflux temperature of the solvent system to yield a homogenous solution. The amount of solvent system was selected to obtain a clear solution aiming at maximal concentration of HyDHC.

The stirring has been stopped and the solution has been cooled down at a cooling rate of 10 K/h to 20° C. respectively to 0° C. (=$T_{cool}$). During the cooling down the solution has been inoculated every 30 minutes by adding individual crystal seeds of HyDHC.

Finally the crystals formed have been separated by filtration over a D3 sintered glass frit under reduced pressure and dried until the weight of the crystals remained constant.

The amount of DDH-HyDHC has been determined in the crystals of HyDHC isolated, respectively in the mother liquor, and indicated as $C_{II,cryst}$ respectively as $C_{II,ML}$ as in table 4.

TABLE 4

Crystallization: Degree of purification at different end temperature of cooling.

| | $T_{cool}$ [° C.] | IPA | | 30 | $C_{II,cryst}$ | $C_{II,ML}$ | $r_{ML/cryst}$ |
|---|---|---|---|---|---|---|---|
| 1 | 20 | IPA | | 30 | 0.38 | 0.94 | 2.5 |
| 2 | 20 | IPA/MeOH (30/5) | | 35 | 0.3 | 1.06 | 3.5 |
| 9 | 0 | IPA | | 30 | 0.31 | 1.64 | 5.3 |

TABLE 4-continued

Crystallization: Degree of purification at different end temperature of cooling.

| | $T_{cool}$ [° C.] | IPA | | 30 | $C_{II,cryst}$ | $C_{II,ML}$ | $r_{ML/cryst}$ |
|---|---|---|---|---|---|---|---|
| 10 | 0 | IPA/MeOH (30/5) | | 35 | 0.34 | 1.21 | 3.6 |

IPA = 2-propanol
MeOH = methanol
$r_{ML/cryst} = C_{II,ML}/C_{II,cryst}$

The results of table 4 show that despite at an end temperature of cooling (=$T_{cool}$) of 20° C. the purification is better for a solvent mixture of methanol and 2-propanol as compared to pure 2-propanol, the situation changes at lower end temperature of cooling. At an end temperature of cooling (=$T_{cool}$) of 0° C. the purification is significantly better for pure 2-propanol as compared to a mixture of 2-propanol and methanol.

Experimental Series 5: Crystallization from Different Alcohols 1 g of HyDHC crystals having an impurity 1.4% DDH-HyDHC (obtained from working up mother liquids of other crystallization experiments) has been dissolved under stirring in the respective amount of the solvent system as indicated in table 5 in a glass flask at reflux temperature of the solvent system to yield a homogenous solution. The amount of solvent system was selected to obtain a clear solution aiming at maximal concentration of HyDHC.

The stirring has been stopped and the solution has been cooled down at a cooling rate of 10 K/h to 0° C. (=$T_{cool}$). During the cooling down the solution has been inoculated every 30 minutes by adding individual crystal seeds of HyDHC.

Finally the crystals formed have been separated by filtration over a D3 sintered glass frit under reduced pressure and dried until the weight of the crystals remained constant.

The amount of DDH-HyDHC has been determined in the crystals of HyDHC isolated, respectively in the mother liquor, and indicated as $C_{II,cryst}$ respectively as $C_{II,ML}$ as in table 5.

TABLE 5

Crystallization from different alcohols.

| Example | Solvent system (vol./vol.) | Volume solvent system [ml] | $C_{II,cryst}$ | $C_{II,ML}$ | $r_{ML/cryst}$ | Yield [%] |
|---|---|---|---|---|---|---|
| Ref. 4 | MeOH | 50 | 1.26% | 1.70% | 1.3 | 79 |
| 11 | EtOH | 30 | 1.12% | 1.52% | 1.4 | 74 |
| 12 | IPA | 30 | 1.04% | 3.32% | 3.2 | 89 |
| 13 | 2BuOH | 25 | 0.98% | 1.28% | 1.3 | 73 |
| Ref. 5 | 1PeOH | 6 | 1.32% | 2.69% | 2.0 | n.d. |

MeOH = methanol,
EtOH = ethanol,
IPA = 2-propanol,
2BuOH = 2-butanol,
1PeOH = 1-pentanol
n.d. = not determined
$r_{ML/cryst} = C_{II,ML}/C_{II,cryst}$ The data of table 5 for Examples 11-13 in accordance with the embodiments of the invention disclosed herein in comparison to the Comparative Examples Ref.4 and Ref.5 not in accordance with the embodiments of the invention disclosed herein, show among alkyl alcohols the choices of suitable alcohols is very limited for obtaining good purification. In this series a high amount of impurity in the starting material has been used to be able to better discriminate between the same class of solvents, i.e., among alcohols. As the experiments of this experimental series have been made in the same manner as experimental series 1, the results of table 5 can be brought in relation to the ones of table 1.

Experimental Series 6: Degree of Purification with Several Crystallization Cycles 11 g HyDHC crystals having an impurity 1.23% DDH-HyDHC was dissolved in 330 ml of 2-propanol at 83° C. and cooled to 0° C. at a cooling rate of 5 K/h. During the cooling down the solution has been inoculated at 70° C. by adding individual crystal seeds of HyDHC. After 30 minutes at 0° C. the crystals formed have been isolated by filtration and dried until the weight of crystals remained constant.

The values found are indicated as $C_{II,cryst}$ respectively as $C_{II,ML}$ respectively yield in table 6.

The crystals isolated have been again dissolved in 2-propanol in a ratio 1 g HyDHC per 30 ml 2-propanol, cooled and isolated at the same manner/conditions as in the first crystallization.

The values found for the second crystallization have been indicated analogously in table 6.

Finally the crystals isolated from the second crystallization have been dissolved, cooled and isolated in the same manner/conditions as in the first crystallization.

The values found for the third crystallization haven been indicated analogously in table 6.

TABLE 6

Degree of purification with several crystallization cycles.

| | $C_{II,cryst}$ | $C_{II,ML}$ | $r_{ML/cryst}$ | Yield [%] | Overall Yield [%] |
|---|---|---|---|---|---|
| Starting crystals | 1.23% | | | | |
| After 1st cryst. | 0.50% | 12.59% | 25.2 | 93 | 93 |
| After 2nd cryst | 0.17% | 6.38% | 37.5 | 95 | 88 |
| After 3rd cryst | 0.05% | 2.22% | 44.4 | 93 | 82 |

$r_{ML/cryst} = C_{II,cryst}/C_{II,ML}$

The results of table 6 show that already a first crystallization is very effective in purifying HyDHC crystals. Further crystallization cycles enhance the degree of purification and very efficiently at high yield with only minor impact on the overall yield. Already after 3 crystallizations cycles a highly impure sample HyDHC has been purified to comprise 0.1% of the impurity DDH-HyDHC.

The invention claimed is:

1. A method for purifying a compound of formula (I) from a composition comprising the compound of formula (I) and a the compound of formula (II) in a solvent system:

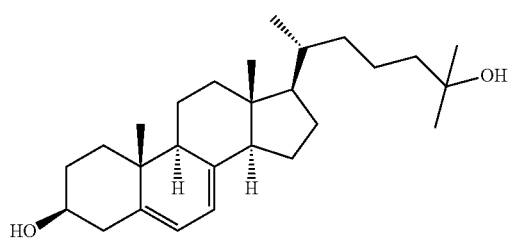

(I)

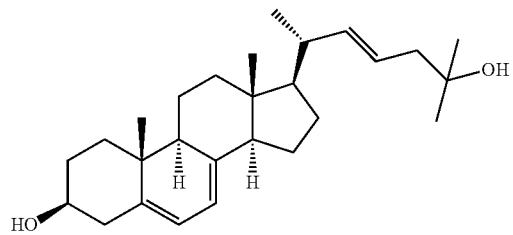

(II)

wherein the method comprises the steps of:
a) dissolving a composition comprising a compound of formula (I) and a compound of formula (II) at temperature ($T_{sol}$) above 40° C. in a crystallization solvent system to yield a solution A comprising the compound of formula (I) and of the compound of formula (II);

b) cooling the solution A comprising the compound of formula (I) and the compound of formula (II) obtained by step a) to a temperature ($T_{cool}$) of 30° C. or below to yield crystals of the compound of formula (I); and c) isolating the crystals of the compound of formula (I), and wherein the solvent system is either:

i) ethanol, 1-propanol, 2-propanol, 2-methyl-1-propanol, 1-butanol or 2-butanol; or ii) a binary, tertiary or quaternary mixture of ethanol, 1-propanol, 2-propanol, 2-methyl-1-propanol, 1-butanol or 2-butanol; or iii) a mixture of solvents selected from the group consisting of ethanol, 1-propanol, 2-propanol, 2-methyl-1-propanol, 1-butanol and 2-butanol with methanol and/or with a $C_5$-$C_6$ alcohol, with the proviso that the total amount of ethanol, 1-propanol, 2-propanol, 2-methyl-1-propanol, 1-butanol and 2-butanol is equal to or more than 50% by weight of the solvent system.

2. The method according to claim 1, wherein the solvent system comprises ethanol, 1-propanol or 2-propanol.

3. The method according to claim 1, wherein the solvent system is 2-propanol.

4. The method according to claim 1, wherein the solvent system comprises a solvent mixture selected from the group consisting of methanol/2-propanol; methanol/1-propanol; methanol/1-propanol/2-propanol and methanol/ethanol/2-propanol.

5. The method according to claim 1, wherein the solvent system comprises a mixture of solvents selected from the group consisting of ethanol, 1-propanol, 2-propanol, 2-methyl-1-propanol, 1-butanol and 2-butanol with methanol and/or with a $C_5$-$C_6$ alcohol, with the proviso that the total amount of ethanol, 1-propanol, 2-propanol, 2-methyl-1-propanol, 1-butanol and 2-butanol is more than 60% by weight.

6. The method according to claim 1, wherein the temperature ($T_{sol}$) in step a) is above 60° C.

7. The method according to claim 1, wherein the temperature ($T_{cool}$) in step b) is in the range of −10° C. to 15° C.

8. The method according to claim 1, wherein the method comprises two or more crystallization cycles.

9. The method according to claim 1, wherein the method of purification results in purifying the compound of formula (I) such that the compound of formula (II) is present as an impurity in an amount of less than 0.40% by weight, relative to the weight of the compound of formula (I).

10. A composition comprising a compound of formula (I) and a compound of formula (II):

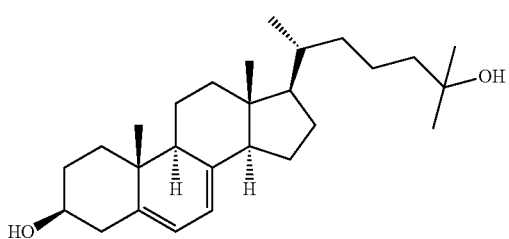

(I)

-continued

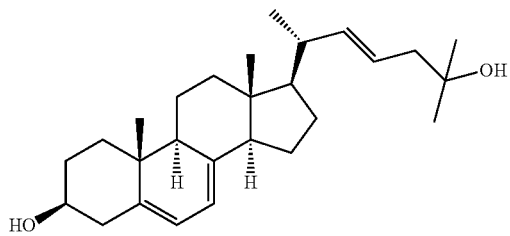

(II)

wherein the amount of the compound of formula (II) in the composition is at most 0.40% by weight, relative to the weight of the compound of formula (I).

11. The method according to claim 1, wherein the temperature ($T_{sol}$) in step a) is at the boiling temperature of the solvent system to at most 10° C. lower than the boiling temperature of the solvent system as measured at 1013 mbar.

12. The method according to claim 11, wherein the temperature ($T_{sol}$) in step a) is at most 5° C. lower than the boiling temperature of the solvent system as measured at 1013 mbar.

13. The method according to claim 1, wherein the temperature ($T_{cool}$) in step b) is in the range of 0° C. to 10° C.

* * * * *